United States Patent [19]

Collman et al.

[11] 3,985,770

[45] Oct. 12, 1976

[54] METHOD OF PRODUCING ALKALI METAL TETRACARBONYLFERRATES AND SOLVATES THEREOF

[75] Inventors: James P. Collman, Stanford; Robert G. Komoto, East Palo Alto, both of Calif.

[73] Assignee: The Board of Trustees of Leland Stanford Junior Unversity, Stanford, Calif.

[22] Filed: June 11, 1973

[21] Appl. No.: 368,495

[52] U.S. Cl............................ 260/340.6; 260/242; 260/270 R; 260/327 R; 260/326.22; 260/329 ME; 260/333; 260/340.3; 260/338; 260/346.1 M; 423/417; 423/418
[51] Int. Cl.²...................................... C07D 319/10
[58] Field of Search................. 260/340.6; 423/417, 423/418

[56] References Cited

UNITED STATES PATENTS

| 1,924,453 | 8/1933 | Muth | 423/417 |
| 3,053,629 | 9/1962 | Pruett et al. | 423/418 |
| 3,232,699 | 2/1966 | Wyman | 423/417 |

*Primary Examiner*—Nicholas S. Rizzo
*Assistant Examiner*—James H. Turnipseed
*Attorney, Agent, or Firm*—Edward B. Gregg

[57] ABSTRACT

Production of alkali metal tetracarbonylferrates by reaction of alkali metal with an iron carbonyl, preferably iron pentacarbonyl, in a suitable solvent and in the presence of an electron carrier, the alkali metal being present in the liquid phase. Also, solvated forms of alkali metal tetracarbonylferrates as new compositions of matter. The alkali metal tetracarbonylferrates are useful in the production of aldehydes, ketones, acids, esters and amides.

8 Claims, No Drawings

METHOD OF PRODUCING ALKALI METAL TETRACARBONYLFERRATES AND SOLVATES THEREOF

The invention described herein was made in the course of work under grants or awards from the National Science Foundation.

This invention relates to a novel and useful method of producing alkali metal tetracarbonylferrates, $M_2Fe(CO)_4$, wherein M is sodium, potassium or a mixture of the two, and it also relates to a novel and useful solvated form of these salts.

Sodium and potassium tetracarbonylferrates are useful, among other things, in the synthesis of aldehydes, ketones, acids, esters and amides. See, for example, papers published by Collman and others in: M. P. Cooke, *J. Amer. Chem. Soc.*, 92, 6080 (1970); J. P. Collman, S. R. Winter and D. R. Clark, ibid, 94, 1788 (1972); J. P. Collman, S. R. Winter and R. G. Komoto, ibid, 95, 249 (1973); J. P. Collman and W. O. Siegl, ibid, 94, 2516 (1972); J. P. Collman, J. N. Cawse and J. I. Brauman, ibid, 94, 5905 (1972); J. P. Collman and Norris W. Hoffman, ibid, 95, 2689 (1973).

As described in co-pending applications of Collman and Winter, Ser. No. 232,247, filed Mar. 6, 1972, now abandoned, entitled "Synthesis of Ketones" and Collman and Winter, Ser. No. 368,496, filed June 11, 1973, now U.S. Pat. No. 3,872,218 issued Mar. 18, 1975 entitled "Synthesis of Alkali Metal Tetracarbonylferrates", an advantageous method of producing alkali metal tetracarbonylferrates is the reaction of the alkali metal with an iron carbonyl, preferably iron pentacarbonyl, in a suitable solvent and in the presence of an electron carrier such as benzophenone or other aromatic ketone, etc. As described in the earlier of the two Collman and Winter patent applications, Ser. No. 232,247, now abandoned this procedure may be carried out by employing sodium or potassium in the solid state in the form of a fine dispersion in an inert liquid such as mineral oil.

While this method works quite well, and has advantages over prior methods such as that described in the Cooke paper cited above, difficulties arise due to the fact that this form of sodium (which is relatively expensive as compared to bulk sodium) becomes encrusted or coated with reaction products or impurities. This encrustation reduces the reactivity of the alkali metal and ultimately causes the reaction to stop. Also, stirring or other agitation of the mixture, which is necessary or advisable, may cause coalescence of the particles of sodium which reduces the reactive surface and therefore reduces the reaction rate. The same considerations apply to potassium and to sodium potassium alloys.

It is an object of the present invention to provide improvements in the synthesis of alkali metal tetracarbonylferrates by the reaction of metallic sodium or potassium or an alloy or mixture of the two with iron carbonyls such as iron pentacarbonyl in the presence of an electron carrier.

It is a particular object of the invention to provide improvements in this method of synthesis, whereby difficulties of the character described, that is to say, the need to employ alkali metal in solid phase and in the form of a fine dispersion, are obviated.

A further object of the invention is to provide novel and useful forms of alkali metal tetracarbonylferrates as new compositions of matter.

The above and other objects of the invention will be apparent from the ensuing description and the appended claims.

We have discovered that the synthesis of alkali metal tetracarbonylferrates by the method referred to above (i.e., by reacting metallic sodium or potassium with an iron carbonyl in the presence of an electron carrier), can be considerably improved by employing the alkali metal (which may be sodium or potassium or an alloy or mixture of the two) in liquid form. This can be done by the choice of a solvent, such as dioxane, which boils at atmospheric pressure above the melting point of sodium, of potassium or of an alloy of the two. Alternatively, a solvent which boils below the melting point of the metal at atmospheric pressure may be employed provided pressure is applied so that the boiling point (under the applied pressure) at least equals and preferably exceeds the melting point of the alkali metal.

This procedure is advantageous because, in the first place, it avoids the need to use finely dispersed sodium in a mineral oil or the like and allows the use of bulk sodium which is much less expensive. The same considerations are applicable to potassium and to alloys and mixture of sodium and potassium.

Secondly, and quite importantly, the reaction proceeds much more efficiently to practical completion because the alkali metal is in the liquid state and is constantly presenting a fresh surface which is not encrusted as are particles of solid sodium or potassium. Normal agitation as by boiling of the solvent and/or bubbling an inert gas such as $N_2$ or CO through the reacting mixture and/or mechanical agitation present adequate surface area of the liquid metal.

An added and very important advantage is that if the solvent employed is one such as dioxane which is capable of coordinating with the alkali metal, a solvated form of salt, $[M_2Fe(CO)_4]_a \cdot [S]_b$, is formed wherein S is the solvent or a co-solvent and a and b are the combining proportions. This aspect of the present invention is discussed in detail below.

In the practice of the present invention, various solvents and electron carriers may be used.

The solvent may function only as a solvent, or as a combined solvent and electron carrier, or as a combined solvent and solvating substance. Without regard to functions other than solvent, suitable examples are as follows: tetrahydrofuran (THF), hexamethylphosphoramide (HMPA), methylpyrrolidone (MP), dimethylformamide (DMF); glyme, diglyme; lower ketones such as; dioxane, lower aliphatic ethers such as dimethyl and diethyl ethers; polyethers such as dimethoxy ether, cellosolve, cyclic polyethers such as dioxane and the crown ethers, lower nitriles such as acetonitrile and propionitrile, tetramethylene sulfone, pyridine, etc. It will be understood that in the above wherever a $C_1$, $C_2$ or $C_3$ alkyl group is identified, higher homologues, e.g., $C_4$ to $C_6$ may be used.

The electron carrier may be any molecule (or mixture of molecules) which is or which contains a strong electron acceptor and which is compatible with the solvent, the reactants, the reagents and the end product. For example, strong oxidizing and/or reducing agents should not be used. Preferably, the electron carrier has at least a moderate solubility in the solvent, although a high solubility is not required. Examples of the electron carrier are as follows:

Aromatic ketones such as benzophenone; 2- and 4-aminobenzophenones; 4-benzoylbiphenyl; o-dibenzoyl benzene; 4,4'-bis-(diethyl-amino) benzophenone; aromatic hydrocarbons such as, naphthalene, anthracene, phenanthrene; aliphatic ketones having fully substituted (tertiary) aliphatic carbon atoms attached to the carbonyl group such as

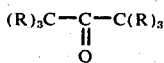

where the R's are the same or different hydrocarbon groups, e.g., methyl; alkyl aryl ketones where the alkyl group likewise has a fully substituted carbon attached to the carbonyl group, such as

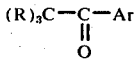

where the R's are as defined above and Ar is an aromatic group, e.g.,

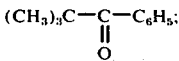

hetero analogues of the aromatic compounds mentioned above, e.g., wherein the pyridine ring is substituted for a benzene ring, as in 2,2'-dipyridyl; 4,4'-dipyridyl; di-2-pyridyl ketone; a variety of other or similar aromatic compounds such as 4-dimethylamino benzophenone; dibenzosuberone; 1,1,2,2-tetraphenylethene; acenaphthalene; benzyl dianil; trimesityl borane; hexamethylphosphortriamide; low molecular weight amines; and diamines such as ethylene diamine (preferably used only at lower temperatures); certain salts having organic cations such as paraquat and diquat [see J.A.C.S., 89, 5562 and Chem. Comm. 1293 (1967)]; decaborane and disodium decaborane; triaryl phosphines such as triphenyl phosphine; cyclo-octadiene,

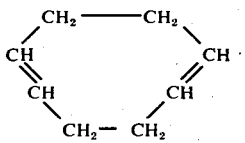

In general, the electron carrier or transfer agent is one which is reasonably soluble in the reaction solvent (and it may also function as the solvent or as a co-solvent); which is compatible with i.e., it is not destructive of the solvent, reactants and desired end product; and it reacts with an alkali metal to form an anion such as the ketones formed from ketones. Such anions result in solutions having a characteristic color, typically a blue color. In general, the electron carrier (identified as A below) is one which accepts an electron from the alkali metal, thus

and which is effective to transfer the electron to the iron carbonyl. The preferred electron carriers are the aromatic ketones and trisubstituted boranes.

The preferred solvating substance is dioxane; see Example 1 below. It is relatively inexpensive such that it may be used as the reaction solvent, it forms the solvated dianion $[Fe(CO)_4]_2 \cdot [S]_3^{4-}$ quantitatively wherein S represents one molecule of dioxane; this solvate is insoluble in the solvent (dioxane), hence is easily recovered as a solid, providing a precipitate; and this solvate, in turn, is quite soluble in preferred solvents for the reactions such as the formation of aldehydes in accordance with the Cooke procedure, alkylation reactions to produce ketones e.g., as follows

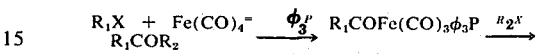

and to form acids, amides and esters in accordance with the following reaction schemes

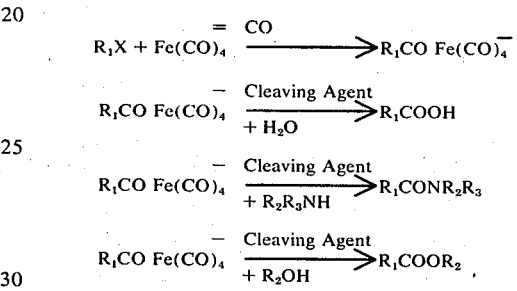

These reactions (formation of aldehydes, ketones, acids, esters and amides) are described in the Cooke and the Collman et al papers cited above and also in the following U.S. Pat. Applications: Collman and Winter, Ser. No. 232,247; now abandoned, and Collman, Winter and Komoto, Ser. No. 293,858 (now abandoned) and 293,859 filed Oct. 2, 1972 issued March 18, 1975 as U.S. Pat. No. 3,872,168. As described in some or all of this literature and in the patent applications, if chlorides such as n-octyl chloride, etc. are used as the alkylating agent (i.e., as $R_1X$ and/or $R_2X$ where X is chlorine), reactivity is less than with bromides, iodides and tosylates and in some cases the use of chlorides is not recommended because of poor yields and/or very slow reaction rates. Yet chlorides, as a class, are the cheapest alkylating agents. One of the important advantages of the dioxane solvate $[Fe(CO)_4]_2 \cdot [S]_3^{4-}$ is that it is much more soluble in certain good solvents, among them THF (the solvate is approximately 14 times more soluble than the non-solvate form in THF), for the various reactions leading to aldehydes, ketones, etc. Being more soluble, these solvates are more reactive and will react much more readily (faster and/or with higher yields) with chloride $R_1X$.

This provides a new class of compounds (omitting the counter ion, which may be $Na^+$ or $K^+$ as produced or another cation by metathesis), $[Fe(CO)_4^=]_a \cdot [S]_b$ wherein a and b are small integers such as 2 and 3, respectively. This results in an inorganic material (the tetracarbonylferrate) in a form which enhances solubility in a variety of organic solvents.

Dioxane is believed to function as a solvating substance by reason of the two oxygen atoms capable of coordination with cations such as the counter ion and/or the $Fe(CO)_4^=$ dianion by reason of its ability to assume a "boat" configuration thus

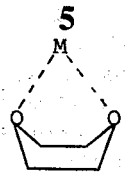

where M represents the metal (alkali metal and/or Fe) to which the coordinate bonds, represented by dashed lines, are directed.

Other organic substances having in common with dioxane the ability to assume a proper steric configuration and having at least two hetero, electronegative atoms (O, N, S, or mixtures thereof) may also be used, examples of which are as follows: 1,4-dioxene, 1,4-dioxin; 0-dimethoxybenzene; dimethoxyethane; trioxane; dibenzo-18-crown-6; dicyclohexyl-18-crown-6; morpholine; p-isoxazine; 2,6-dimethylmorpholine; N-methylmorpholine; piperazine; N,N'-dimethylpiperazine; 2,5-dimethylpiperazine; 2,6-dimethylpiperazine; 1,4-diazabicyclo[2,2,2]octane; 1,10-phenanthroline; 2,2'-dipyridyl; tetramethylethylene diamine(TMEDA); 1,4-thioxane; dithiane; hexamethylphosphorictriamide (HMPA).

These compounds (or mixtures thereof including dioxane as a component of mixtures) may be employed. Where the selected compound, as in the case of dioxane, is sufficiently inexpensive and is a good reactive solvent for the reaction leading to the desired solvate, it may be used as the reaction solvent; and where used as the solvent and if the solvate remains dissolved in the reaction mixture, the resulting solution may be used directly in reactions with halides, etc. to produce aldehydes, ketones, etc. without isolating an intermediate solvate. If the solvating substance is a poor solvent for the reduction of iron carbonyl to form the solvated tetracarbonylferrate, and/or if the solvating substance is very expensive, it may be used in stoichiometric amount to form the solvate, thus

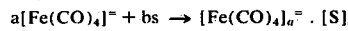

or in excess of desired, in a suitable solvent such as THF or any of those mentioned above which is compatible.

The following specific examples will serve further to illustrate the practice and advantages of the invention.

EXAMPLE 1

Preparation of Salt in Solvated Form by Use of a High Boiling Point Solvent

To dry, degassed dioxane was added 23 g (1.0 mole) sodium in 8 chunks. Then 18.2 g benzophenone was added whereupon a blue color formed indicating the formation of the sodiumbenzophenone ketyl, Na⁺[-φCOφ]⁻. The dioxane was allowed to reflux for 10-15 minutes then with the stirrer on full power, 40 ml Fe(CO)₅ were added over 30 minutes. The last 27 ml of Fe(CO)₅ were added over 20 minutes and the reaction stirred 1 hour, when no blue color was observed. The resulting precipitate was filtered using special glass frit and the dioxane filtered into a holding flask for another prep. The ppt was washed three times (1500 ml) with petroleum ether and then pumped on at about 1mm/30°-50° C to remove the last traces of petroleum ether. The product was a white powder.

By gas chromatographic and nmr techniques, it was determined that this powder was (except for a very small amount of impurities which do not interfere with its use for purposes of synthesizing aldehydes, ketones, etc. as described in the literature references above) a solvated form of disodium tetracarbonylferrate having the ferrate and dioxane in the molecule in the proportions of 2 and 3, respectively, thus

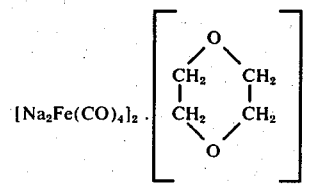

The molecular weight is 346.

The analysis employed the quantitative reaction (omitting the dioxane component, which does not enter into the reactions)

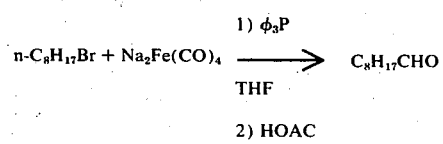

This reaction is carried out in the manner described in the Cooke paper cited above. Excess triphenyl phosphine and n-octyl bromide were added to THF containing a weighed amount of the disodium salt. The reaction was allowed to proceed 2 to 3 hours at room temperature under nitrogen, the reaction mixture was quenched with acetic acid and the amount of nonanal was determined by gas chromatography using dodecane as internal standard by reference to previous standardization with nonanal. The purity of the product (i.e., the solvated tetracarbonylferrate) was determined in this manner and from the purity, the yield was determined. Purity and yield were about 95-100% and 80-100%, respectively. Analytical data were as follows:

Gas chromatographic analysis: Using a 3 meter-¼'- 10% carbowax column at 120° C, 1,4-dioxane was determined by co-injection to be incorporated as a solvate in a sample of Na₂Fe(CO)₄ prepared in 1,4-dioxane.

When a 346 mg sample of the Na₂Fe(CO)₄ 1,4-dioxane solvate was gas chromatographed with n-tridecane as an internal standard, it was determined that 132 mg (1.5mmol) of 1,4-dioxane and 214 mg (1.0mmol) of Na₂Fe(CO)₄ were in the sample.

Thus the ratio of Na₂Fe(CO)₄ to 1,4-dioxane is 2 to 3.

Proton magnetic resonance analysis: A sample of the Na₂Fe(CO)₄ 1,4-dioxane solvate dissolved in d₆-acetone and standardized with benzene as an internal reference gave the spectrum as follows: δ7.27, C₆H₆; δ3.57, 1,4-dioxane. Upon integration of the two peaks it was determined that the ratio of Na₂Fe(CO)₄ to 1,4-fioxane in the sample is 2 to 3.

1,4-Dioxane is usually found at δ3.64, but the slight up-field shift is due to the presence of the Na₂Fe(CO)₄.

EXAMPLE 2

Preparation of Same Salt by Use of a Low Boiling Solvent Under Pressure

Using a Fisher-Porter bottle, 0.86 g (37.4 mmol) of solid sodium metal and 2.91 g (16 mmol) of benzophenone were added to 40 ml of dry, degassed THF under $N_2$ flow. The reaction turned blue, characteristic of the ketyl. The Fisher-Porter bottle was then pressured up to 43 psi over atmospheric with CO and the whole reaction stirred vigorously using a magnetic stirrer at 120°. At this pressure THF can reach temperatures in excess of 100° before boiling. The reaction was cooled to 60° and 2.25 ml (16.8 mmol) of $Fe(CO)_5$ was added. A white precipitate remained after addition of n-hexane. Washing the white precipitate and pumping to dryness gave a product that yielded 92% nonanal based on 214 MW for $Na_2Fe(CO)_4$. The product of this example was not solvated.

EXAMPLE 3

Preparation of Mixed Na and K Tetracarbonylferrates by the Use of a Sodium Potassium Alloy The 29% potassium K-Na alloy was prepared by melting 4.4 g (192 mmol) sodium and 1.5 g (38 mmol) potassium in boiling xylene. The alloy was then allowed to resolidify and then was added to the reaction vessel. The reaction was carried out using 250 ml of refluxing THF, 3.6 g (20 mmol) benzophenone and the K-Na alloy.

$Fe(CO)_5$ (13.5 ml, 100 mmol) dissolved in 20 ml of THF was added over 50 minutes. The reaction was allowed to stir for 2 hours and worked up in the usual fashion. An 81.2 yield of mixed Na and K (or Na-K) tetracarbonylferrate resulted. Titer on this anion gave a quantative yield of nonanal based on an average MW of 220.

The alkali metal tetracarbonylferrates are sensitive to water and oxygen, therefore should be kept in non-aqueous environments and free from air. If other metal tetracarbonylferrates are desired, they may be produced from the alkali metal species by metathesis. For example, the sodium salt in THF may be treated with lithium bromide to produce sodium bromide, which is insoluble in THF, and lithium tetracarbonylferrate in solution in THF. The temperature at which the reaction of alkali metal with iron carbonyl is carried out may vary considerably, e.g., from room temperature (25° C) or lower to 100° C or higher. Low temperatures tend to reduce reaction rates and/or to reduce the solubility of reactants while high temperatures tend to degrade the electron carrier or its anion.

It will therefore be seen that a new and improved method of producing tetracarbonylferrate salts and new and useful forms of such salts have been provided.

We claim:

1. In the method of producing alkali metal tetracarbonylferrates having the formula $M_2Fe(CO)_4$ wherein M is sodium, potassium or a mixture or alloy of the two by reacting the alkali metal M with an iron carbonyl in a solvent and in the presence of an electron carrier which functions to accept an electron from the alkali metal thus $$M+A \rightarrow M^+ +A^-$$

wherein A is the electron carrier and M is the alkali metal, said electron carrier A in its ionized form $A^-$ being capable of transferring an electron to the iron carbonyl and thereby regenerating the electron carrier A for further such electron transfer, the improvement which comprises conducting such reaction of alkali metal with iron carbonyl and so catalyzed by said electron carrier at a temperature such that the alkali metal is in the liquid state.

2. The improvement of claim 1 wherein the iron carbonyl is iron pentacarbonyl.

3. The improvement of claim 2 wherein the reaction is carried out in a solvent which has a boiling point at atmospheric pressure in excess of the melting point of the alkali metal M, and the reaction is carried out at such boiling point.

4. The improvement of claim 3 wherein M is sodium.

5. The improvement of claim 3 wherein the solvent includes at least a substantial proportion of dioxane.

6. The improvement of claim 2 wherein the reaction is carried out under superatmospheric pressure.

7. The improvement of claim 2 wherein the solvent has a boiling point at atmospheric pressure which is below the melting point of the alkali metal M and the reaction is carried out under superatmospheric pressure and at a temperature above the melting point of M.

8. The improvement of claim 7 wherein M is sodium.

* * * * *